(12) United States Patent
Carter et al.

(10) Patent No.: US 10,888,857 B2
(45) Date of Patent: Jan. 12, 2021

(54) IONIC LIQUID CATALYST REGENERATION WITH REDUCED HYDROGEN AMOUNTS (71) Applicant: UOP LLC, Des Plaines, IL (US)

(72) Inventors: Elizabeth Carter, Arlington Heights, IL (US); Douglas A. Nafis, Mount Prospect, IL (US); Bong-Kyu Chang, Novato, CA (US); Hye Kyung Timken, Albany, CA (US); Huping Luo, Moraga, CA (US); Michael Girgis, Richmond, CA (US)

(73) Assignee: UOP LLC, Des Plaines, IL (US)

( * ) Notice: Subject to any disclaimer, the term of this patent is extended or adjusted under 35 U.S.C. 154(b) by 103 days.

(21) Appl. No.: 16/010,695

(22) Filed: Jun. 18, 2018

(65) Prior Publication Data
US 2019/0381493 A1 Dec. 19, 2019

(51) Int. Cl.
C07C 2/58 (2006.01)
B01J 38/10 (2006.01)
B01J 31/02 (2006.01)
B01J 31/40 (2006.01)
C07C 2/60 (2006.01)
C07C 2/56 (2006.01)

(52) U.S. Cl.
CPC ........... B01J 38/10 (2013.01); B01J 31/0284 (2013.01); B01J 31/0298 (2013.01); B01J 31/4015 (2013.01); C07C 2/60 (2013.01); C07C 2531/02 (2013.01)

(58) Field of Classification Search
USPC ........................................ 585/709, 721, 727
See application file for complete search history.

(56) References Cited

U.S. PATENT DOCUMENTS

| 7,651,970 | B2 | 1/2010 | Elomari et al. |
| 7,691,771 | B2 | 4/2010 | Harris et al. |
| 7,825,055 | B2 | 11/2010 | Elomarie et al. |
| 8,237,004 | B2 | 8/2012 | Timken et al. |
| 9,212,321 | B2 | 12/2015 | Timken et al. |
| 9,233,316 | B2 | 1/2016 | Timken et al. |

(Continued)

FOREIGN PATENT DOCUMENTS

| CN | 206715936 U | 12/2017 |
| KR | 101636373 B1 | 7/2016 |
| WO | 2017132016 A1 | 8/2017 |

OTHER PUBLICATIONS

International Search Report from PCT application No. PCT/US2019/037595, dated Sep. 19, 2019.

(Continued)

Primary Examiner — James E McDonough (57) ABSTRACT

Processes for regenerating ionic liquid catalyst by contacting the ionic liquid catalyst with hydrogen gas in a regeneration reactor. The amount of hydrogen is less than 550 SCF/BBL (97.96 m$^3$/m$^3$) of spent ionic liquid catalyst, or less than 500 SCF/BBL (89.05 m$^3$/m$^3$) of spent ionic liquid catalyst, or between 550 and 45 SCF/BBL (97.96 and 8.015 m$^3$/m$^3$) of spent ionic liquid catalyst, or between 500 and 50 SCF/BBL (89.05 and 8.905 m$^3$/m$^3$) of spent ionic liquid catalyst. Alkylation processes are also disclosed.

20 Claims, 2 Drawing Sheets (56) References Cited

U.S. PATENT DOCUMENTS

| | | | |
|---|---|---|---|
| 9,254,450 B2 | 2/2016 | Timken et al. | |
| 9,320,199 B2 | 4/2016 | Timken et al. | |
| 9,802,186 B2 | 10/2017 | Luo et al. | |
| 2007/0142213 A1* | 6/2007 | Elomari | B01J 27/30 502/53 |
| 2010/0197483 A1* | 8/2010 | Elomari | B01J 31/403 502/164 |
| 2014/0037512 A1* | 2/2014 | Timken | C07C 2/58 422/187 |
| 2017/0216827 A1 | 8/2017 | Girgis et al. | |

OTHER PUBLICATIONS

Written Opinion from PCT application No. PCT/US2019/037595, dated Sep. 19, 2019.
Beskov, VS, et al, excerpt from General Chemical Technology and Basis of Industrial Ecology, 1999, pp. 182-183.
Zefirov, N.S., excerpt from Chemical Encyclopedia, 1995, vol. 4, col. 452.
International Search Report from PCT application No. PCT/US2019/037594, dated Oct. 17, 2019.
Written Opinion from PCT application No. PCT/US2019/037594, dated Oct. 17, 2019.

* cited by examiner

IONIC LIQUID CATALYST REGENERATION WITH REDUCED HYDROGEN AMOUNTS

FIELD OF THE INVENTION

This invention relates generally to ionic liquid regeneration processes, and more specifically to ionic liquid regeneration processes that use a lower amount of hydrogen, and even more particularly to alkylation processes that utilize the ionic liquid catalyst and regenerate the ionic liquid catalyst with hydrogen.

BACKGROUND OF THE INVENTION

Commercially, the alkylation of isoparaffins has been catalyzed by acids such as sulfuric acid and hydrofluoric acid. Conjunct polymer (acid soluble oils, (ASO) also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

Recently, there has been a desire to replace the use of sulfuric acid and hydrofluoric acid with more environmentally friendly materials. One such solution utilizes acidic ionic liquids as catalysts in hydrocarbon conversion processes, such as alkylation, isomerization, disproportionation, reverse disproportionation, and oligomerization. The ionic liquid catalysts are more environmentally friendly and therefore, more desirable than the sulfuric acid and hydrofluoric acid.

However, just as with the sulfuric acid and hydrofluoric acid, conjunct polymers are byproducts of the hydrocarbon reactions using ionic liquids. The conjunct polymers form a complex with the ionic liquid catalyst. The ionic liquid catalyst loses its effectiveness over time as the amount of conjunct polymer increases. Over time, the ionic liquid catalyst must then either be replaced or regenerated. Since ionic liquids are typically relatively expensive, efficient and effective processes for regenerating the ionic liquid catalysts are desired.

One process for regenerating the spent ionic liquid catalyst involves reducing the amount of conjunct polymer from the ionic liquid catalyst by contacting the spent ionic liquid catalyst with hydrogen gas. The contacting of spent ionic liquid catalyst with hydrogen gas takes place either on the surface of solid hydrogenation catalyst or in absence of solid hydrogenation catalyst. In processes conducted in the absence of a solid hydrogenation catalyst, the spent ionic liquid is contacted with hydrogen with sufficient and efficient mixing such as agitating, baffling, stirring, shaking, bubbling or any other methods (or combinations thereof). In regeneration processes, a content of conjunct polymer in spent ionic liquid catalyst is reduced to produce a regenerated ionic liquid catalyst which is recycled back to reaction zone.

Due to the beneficial nature of utilizing ionic liquid catalyst in hydrocarbon conversion reactions, including alkylation reactions, there is an ongoing and continuous need for efficient and effective processes for regenerating spent ionic liquid catalyst.

SUMMARY OF THE INVENTION

It has been discovered that the hydrogen gas used to regenerate the spent ionic liquid catalyst be reduced from what is currently utilized. Conventional hydroprocessing processes recycle hydrogen gas to provide a large excess of hydrogen above the stoichiometric requirements, typically in the range of 1,500-15,000 SCF/BBL (approximately 267.2 to 2,672 $m^3/m^3$). However, it was surprisingly discovered that conjunct polymer is removed effectively and efficiently from spent ionic liquid catalyst in a regeneration process while utilizing a much lower amount of hydrogen.

In view of the reduced amount of hydrogen, various processes for regenerating spent ionic liquid catalyst have also been invented. The processes either use a once through stream of hydrogen gas or utilize a single stage compressor for a recycle hydrogen gas. Either process does not require a complex or expensive process for separation and recovery of hydrogen chloride.

Therefore, the present invention may be characterized, in at least one aspect, as providing a process for regenerating spent ionic liquid catalyst by contacting spent ionic liquid catalyst with hydrogen in a reactor, the reactor operating at conditions sufficient to reduce an amount of conjunct polymer in the spent ionic liquid catalyst to provide a regenerated ionic liquid catalyst, wherein an amount of hydrogen is less than 550 SCF/BBL (97.96 $m^3/m^3$) of spent ionic liquid catalyst.

It is contemplated that the amount of hydrogen is between 550 and 45 SCF/BBL (97.96 and 8.015 $m^3/m^3$) of spent ionic liquid catalyst.

It is further contemplated that the amount of hydrogen is less than 500 SCF/BBL (89.05 $m^3/m^3$) of spent ionic liquid catalyst.

It is also contemplated that the amount of hydrogen is between 500 and 50 SCF/BBL (89.05 and 8.905 $m^3/m^3$) of spent ionic liquid catalyst.

It is contemplated that an operating temperature of the reactor is between approximately 93.3 and 343° C. (200 and 650° F.).

It is further contemplated that an operating pressure of the reactor is between approximately 344.7 and 34,470 kPa (50 and 5,000 psig).

It is contemplated that the contacting of the spent ionic liquid catalyst and the hydrogen occurs in the presence of a solid regeneration catalyst.

Alternatively, it is contemplated that the contacting of the spent ionic liquid catalyst and the hydrogen occurs in the absence of a solid regeneration catalyst. Accordingly, contacting includes agitating a mixture of the spent ionic liquid and the hydrogen within the reactor.

The present invention may also be broadly characterized as providing a process for regenerating spent ionic liquid catalyst by removing conjunct polymer from the spent ionic liquid catalyst which includes: passing a stream of spent ionic liquid catalyst stream to a regeneration zone, the regeneration zone comprising at least one reactor vessel and the stream of spent ionic liquid catalyst comprising conjunct polymer; passing a stream of hydrogen gas into the regeneration zone, wherein an amount of hydrogen gas passed to the regeneration zone comprises less than 550 SCF/BBL (97.96 $m^3/m^3$) of spent ionic liquid catalyst passed to the regeneration zone; contacting the conjunct polymer from the stream of spent ionic liquid catalyst with the hydrogen gas in the regeneration zone; and, recovering a regenerated ionic liquid catalyst stream comprising less conjunct polymer than the stream of spent ionic liquid catalyst.

It is contemplated that the contacting of the spent ionic liquid and the hydrogen gas occurs in the presence of a solid regeneration catalyst.

Again, it is alternatively contemplated that the contacting of the spent ionic liquid and the hydrogen occurs in the absence of a solid regeneration catalyst. Accordingly, the contacting includes agitating a mixture of the spent ionic liquid and the hydrogen gas within the reaction zone.

It is contemplated that the process also includes injecting the stream of hydrogen gas into the stream of spent ionic liquid catalyst to form a combined stream and injecting the combined stream into the at least one reactor of the regeneration zone.

It is further contemplated the amount of hydrogen passed to the regeneration zone is between 550 and 45 SCF/BBL (97.96 and 8.015 $m^3/m^3$) of spent ionic liquid catalyst passed to the regeneration zone.

It is also contemplated the amount of hydrogen passed to the regeneration zone is less than 500 SCF/BBL (89.05 $m^3/m^3$) of spent ionic liquid catalyst passed to the regeneration zone.

It is contemplated the amount of hydrogen passed to the regeneration zone is between 500 and 50 SCF/BBL (89.05 and 8.905 $m^3/m^3$) of spent ionic liquid catalyst passed to the regeneration zone.

It is further contemplated an operating temperature of the reactor is between approximately 93.3 and 343° C. (200 and 650° F.).

It is also contemplated an operating pressure of the reactor is between approximately 344.7 and 34,470 kPa (50 and 5,000 psig).

In yet another aspect of the present invention, the present invention may be broadly characterized as providing an alkylation process which includes: passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an alkylate effluent; separating the alkylate effluent from spent ionic liquid catalyst in a separation zone; passing a stream of the spent ionic liquid catalyst to a regeneration vessel in a regeneration zone, wherein the spent ionic liquid catalyst includes conjunct polymer; passing hydrogen into the regeneration vessel of the regeneration zone, wherein an amount of hydrogen gas passed to the regeneration zone comprises less than 550 SCF/BBL (97.96 $m^3/m^3$) of spent ionic liquid catalyst passed to the regeneration zone; contacting the hydrogen with the conjunct polymer in the regeneration vessel; and, passing a stream of regenerated ionic liquid catalyst from the regeneration zone to the reaction zone, wherein the regenerated ionic liquid catalyst comprises less conjunct polymer than the spent ionic liquid catalyst.

In still another aspect of the present invention, the present invention may be generally characterized as providing a process for regenerating spent ionic liquid catalyst by removing conjunct polymer from the spent ionic liquid catalyst by: operating a reaction vessel under conditions sufficient to perform, in the presence of an ionic liquid catalyst, a hydrocarbon conversion reaction and provide a reaction effluent; separating the reaction effluent into a hydrocarbon phase and a spent ionic liquid catalyst, wherein the spent ionic liquid catalyst includes conjunct polymer; contacting the spent ionic liquid catalyst with hydrogen in a regeneration zone at conditions sufficient to reduce an amount of conjunct polymer in the spent ionic liquid catalyst to provide a regenerated effluent; separating the regenerated effluent into a liquid phase comprising regenerated ionic liquid catalyst and a vapor phase comprising hydrogen and hydrogen chloride; separating the hydrocarbon phase into a plurality of liquid hydrocarbon streams; and, isolating the vapor phase from the liquid hydrocarbon streams.

It is contemplated that the process includes removing the hydrogen chloride from the vapor phase in a scrubber.

It is also contemplated that the process includes compressing a portion of the vapor phase in a single stage compressor to provide a compressed vapor phase and combining the compressed vapor phase with the spent ionic liquid catalyst, wherein the compressed vapor phase does not pass through a process for HCl separation between being compressed in the single stage compressor and being combined with the spent ionic liquid catalyst.

It is contemplated that the hydrocarbon conversion reaction comprises an alkylation reaction. The plurality of liquid hydrocarbon streams may include at least one recycle stream to the reaction vessel, and one alkylate product stream. The hydrocarbon phase may also be separated into at least one vapor stream. The at least one vapor stream may be combined with the at least one recycle stream.

It is further contemplated that the spent ionic liquid catalyst is contacted with the hydrogen in the regeneration zone in the presence of a hydrogenation catalyst.

It is also contemplated that the spent ionic liquid catalyst is contacted with the hydrogen in the regeneration zone in the absence of a solid regeneration catalyst.

In another aspect of the present invention, the present invention may be broadly characterized as providing a process for regenerating spent ionic liquid catalyst by removing conjunct polymer from the spent ionic liquid catalyst which includes: passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an effluent stream; separating the effluent stream in a separation zone into a hydrocarbon stream and a spent ionic liquid catalyst stream, wherein the spent ionic liquid catalyst stream includes conjunct polymer; passing a stream of the spent ionic liquid catalyst to a regeneration vessel in a regeneration zone; reducing an amount of the conjunct polymer in the spent ionic liquid catalyst with hydrogen in a regeneration vessel to provide a regeneration effluent comprising regenerated ionic liquid catalyst; passing a stream of the regeneration effluent to a separation vessel configured to separate the regenerated effluent into a liquid phase comprising the regenerated ionic liquid catalyst and a vent gas stream comprising hydrogen and hydrogen chloride; and, passing a recycle stream comprising the regenerated ionic liquid catalyst to the reaction zone.

It is contemplated that the amount of the conjunct polymer in regenerated ionic liquid catalyst is reduced with hydrogen in the presence of a hydrogenation catalyst.

It is also contemplated that the amount of the conjunct polymer in regenerated ionic liquid catalyst is reduced with hydrogen in the absence of a hydrogenation catalyst.

It is contemplated that the process also includes compressing a portion of the vent gas stream in a single stage compressor to provide a compressed vapor stream and passing the compressed vapor stream to the regeneration vessel, wherein the compressed vapor phase does not pass through a process for HCl separation between being compressed in the single stage compressor and being combined with the spent ionic liquid catalyst.

It is further contemplated that the process also includes venting a portion of the recycle vapor stream before passing the regenerated ionic liquid catalyst to the reaction vessel.

It is also contemplated that the process also includes removing the hydrogen chloride from the vent gas stream in a scrubber.

In yet another aspect of the present invention, the present invention may be broadly characterized as providing a process for regenerating spent ionic liquid catalyst by removing conjunct polymer from the spent ionic liquid catalyst which includes: passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an effluent stream; separating the effluent stream in a separation zone to provide a hydrocarbon stream and a spent ionic liquid catalyst stream, wherein the spent ionic liquid catalyst stream includes spent ionic liquid catalyst and conjunct polymer; passing the spent ionic liquid catalyst stream to a regeneration vessel in a regeneration zone; reducing an amount of the conjunct polymer in the spent ionic liquid catalyst with hydrogen in a regeneration vessel to provide a regeneration effluent; passing a stream of the regeneration effluent to a separation vessel configured to separate the regenerated effluent into a liquid phase comprising regenerated ionic liquid catalyst and a vent gas stream comprising hydrogen and hydrogen chloride; separating the hydrocarbon stream in a product recovery zone into a plurality of liquid hydrocarbon streams and at least one vapor stream; combining at least one of the liquid hydrocarbon stream and the at least one vapor stream to provide a combined recycle stream; and, passing the combined recycle stream to the reaction vessel in the reaction zone, wherein the at least one vapor stream does not pass through a process for HCl separation between being separated in the product recovery zone and being combined with the liquid hydrocarbon stream.

It is contemplated that the product recovery zone comprises at least one distillation column configured to provide at least two liquid hydrocarbon streams and an overhead stream. The process may include passing the overhead stream to an HCl Stripper configured to provide at least one of the liquid hydrocarbon streams and the at least one vapor stream. The at least one liquid hydrocarbon stream from the product recovery zone may be combined with the at least one vapor stream from the HCl Stripper. The at least two liquid hydrocarbon streams may comprise an alkylate stream and an isobutane recycle stream.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, it has been discovered that the amount of hydrogen gas fed to an ionic liquid regeneration process may be significantly reduced. Current hydroprocessing processes with a recycle compressor typically use between 1,500 and 15,000 SCF/BBL (approximately 267.2 to 2,672 $m^3/m^3$). In comparison to conventional hydroprocessing processes, the processes according to the present invention add hydrogen gas to a regeneration section at rate of less than 550 SCFB (97.96 $m^3/m^3$).

This surprising and unexpected result allows for the elimination of a complex recycle compressor and provides for processes that employ a once-through hydrogen regeneration process. The purpose of the recycle compressor in such regeneration processes associated with an alkylation reaction is to provide recycle gas flow for the hydro-regen reactor and to compress the off-gas from the fractionation columns so that hydrogen chloride (HCl) is recovered in an absorber. The second purpose requires two stages of compression. The present invention allows for recovery and recycle of HCl without a two-stage compressor.

There is a significant cost-saving benefit from utilizing a once-through hydrogen regeneration process since the complex recycle compressor is eliminated. Additionally, the HCl Absorber for the recycled gas in conventional processes, and associated equipment, can also be eliminated. The elimination of this equipment provides significant cost savings without requiring a large increase in required chloride makeup rate.

In one or more embodiments, the excess hydrogen is vented, and off-gas can be passed to a scrubber at regeneration flash drum. As mentioned above, the recycle compressor, compressor drums/coolers, and HCl Absorber can be eliminated in the present processes. Additionally, the HCl stripper off-gas, which is rich in hydrogen chloride, can be routed to the isobutane recycle, since all non-condensables are soluble in the isobutane recycle. Depropanizer bottoms (or HCl stripper bottoms) are also routed to the isobutane recycle. A small vent is added to the scrubber at isostripper overhead receiver. Additionally, a small vent is added to scrubber at the ionic liquid surge drum to decrease the pressure of the ionic liquid surge drum in order to vent hydrogen soluble in ionic liquid prior to entering alky reactor. The results of the present designs allow the elimination of the compressor and HCl absorber without large HCl loss from either the fractionation section or hydro-regen section. The isostripper sidecut receiver remains 100% liquid phase even with C2 and HCl recycle from the HCl stripper, preventing non-condensables venting with large HCl loss. Soluble hydrogen returning with the regenerated ionic liquid from the regeneration section can be vented in small amounts at the ionic liquid surge drum and isostripper overhead receiver without an intolerable HCl loss from the system.

With these general principles in mind, one or more embodiments of the present invention will be described with the understanding that the following description is not intended to be limiting.

Figure 1:
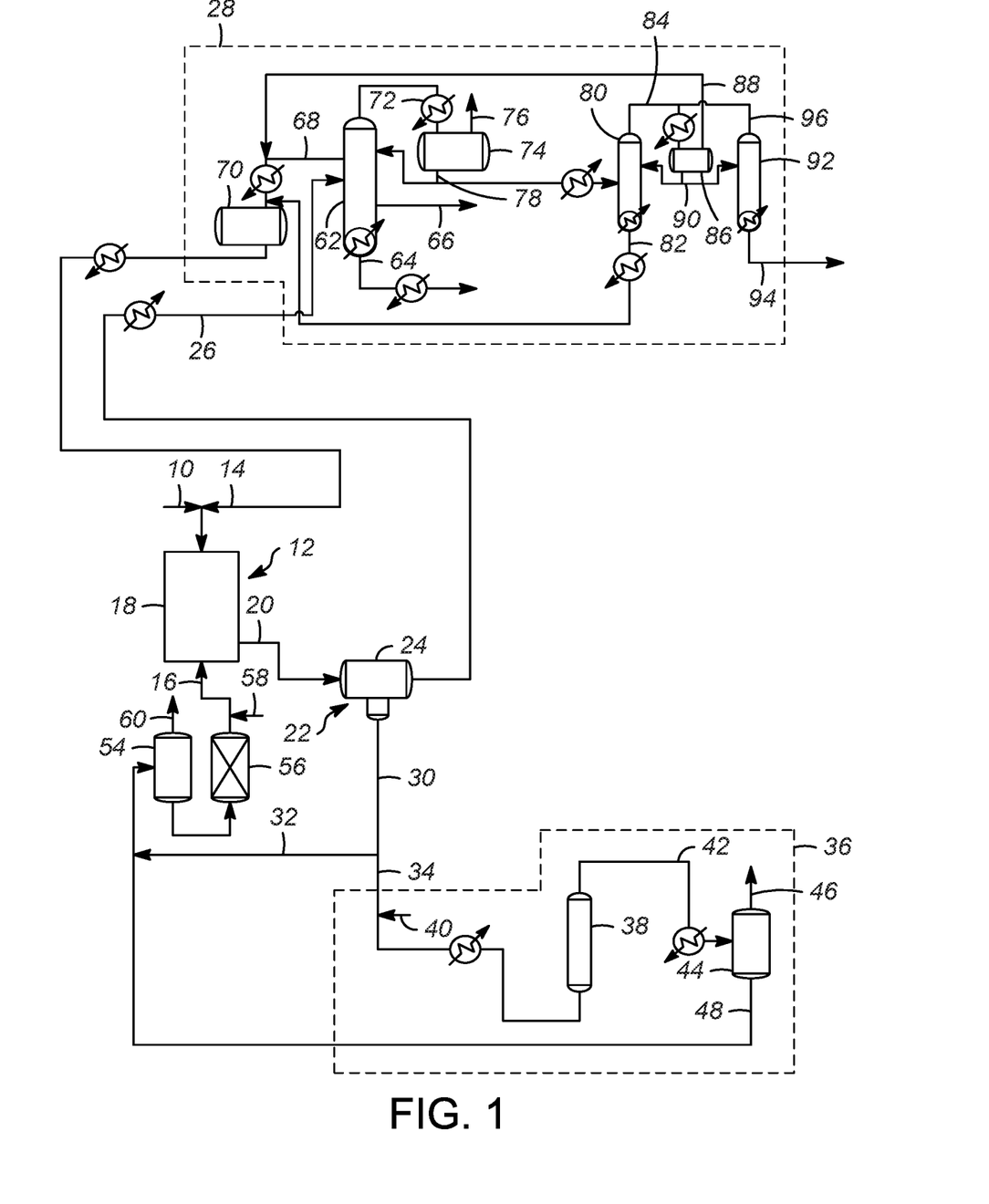
FIG. 1 shows a schematic process flow diagram according to one or more embodiments of the present invention; and, FIG. 2 shows another schematic process flow diagram according to one or more embodiments of the present invention.
Figure 2:
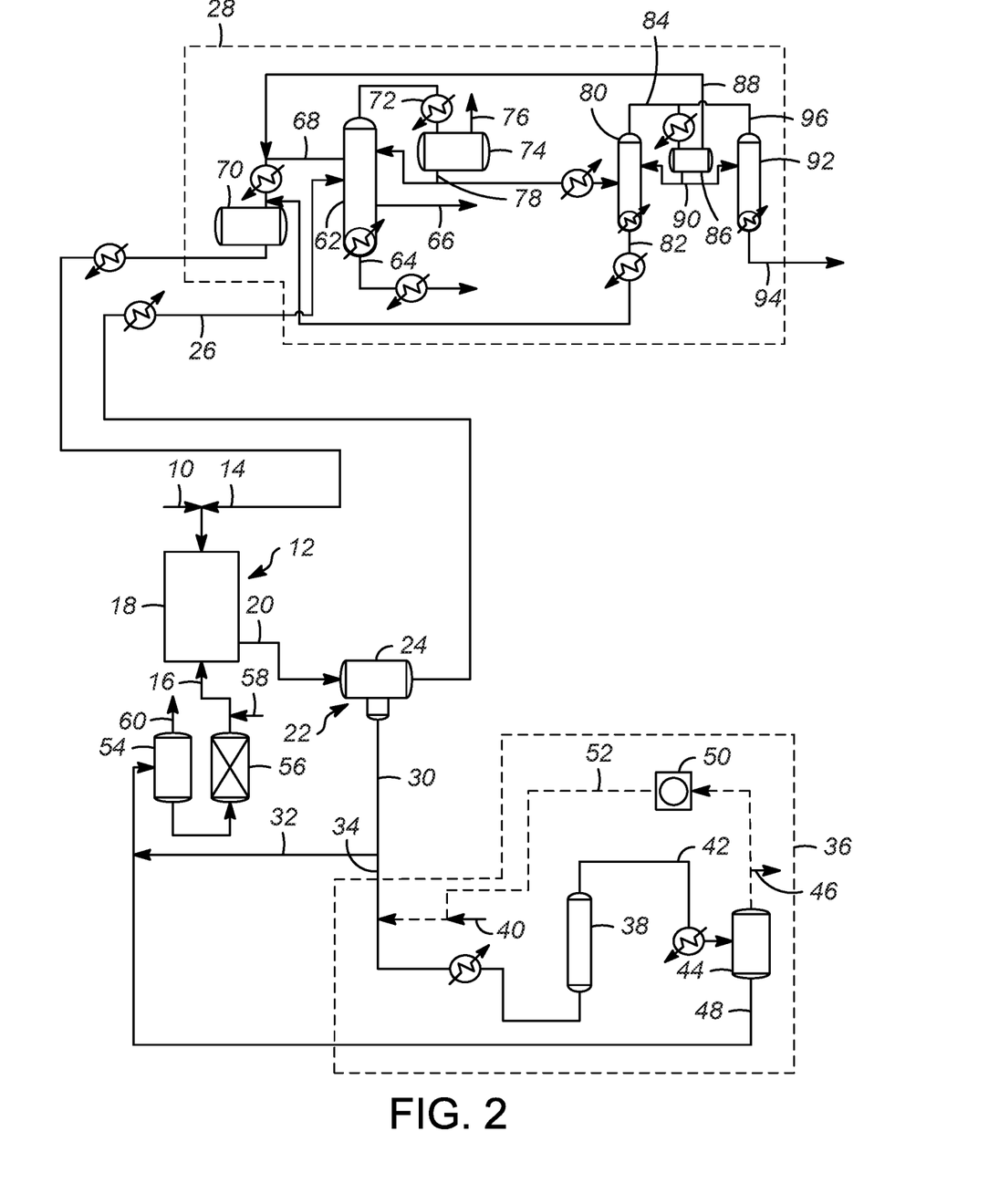

Accordingly, with reference to FIGS. 1 and 2, a hydrocarbon feed 10 is passed into a reaction zone 12. The hydrocarbon feed 10 typically includes a mixture of olefins, paraffins, and isoparaffins, and they may be separately added to the reaction zone 12 in one or more locations. Thus, the hydrocarbon feed 10 comprises an olefin stream of olefins. Additionally, an isoparaffin stream of isoparaffins 14 is also passed to the reaction zone 12. An ionic liquid stream 16 is also passed to the reaction zone 12. The reaction zone 12 includes at least one reactor 18 for an alkylation reaction.

In general, an alkylation process includes passing an isoparaffin and an olefin to an alkylation reactor, where the alkylation reactor 18 includes an ionic liquid catalyst to react the olefin with the isoparaffin to generate an alkylate. The paraffin used in the alkylation process preferably comprises an isoparaffin having from 4 to 10 carbon atoms, or 4 to 8 carbon atoms, or 4 to 5 carbon atoms. The olefin used in the alkylation process preferably has from 2 to 10 carbon atoms, or 3 to 8 carbon atoms, or 3 to 5 carbon atoms. The isoparaffin has from 4 to 10 carbon atoms, and the olefin has from 2 to 10 carbon atoms. According to one or more embodiments of the present invention, the alkylation process upgrades relatively low value C4 hydrocarbons to higher value alkylates. To that extent, one specific embodiment is the alkylation of butanes with butylenes to generate C8 compounds. Preferred products include trimethylpentane (TMP), and while other C8 isomers are produced, one competing isomer is dimethylhexane (DMH). The quality of the product stream can be measured in the ratio of TMP to DMH, with a high ratio desired.

Typical alkylation reaction conditions include a temperature in the range of about −20° C. (−4° F.) to the decomposition temperature of the ionic liquid, or about −20° C. (−4° F.) to about 100° C. (212° F.), or about −20° C. (−4° F.) to about 80° C. (176° F.), or about 0° C. (32° F.) to about 80° C. (176° F.), or about 20° C. (68° F.) to about 80° C. (176° F.), or about 20° C. (68° F.) to about 70° C. (158° F.), or about 20° C. (68° F.) to about 50° C. (122° F.). Ionic liquids can also solidify at moderately high temperatures, and therefore it is preferred to have an ionic liquid that maintains its liquid state through a reasonable temperature span. In some embodiments, cooling may be needed. If cooling is needed, it can be provided using any known methods. The pressure is typically in the range of atmospheric (0.1) to about 8.0 MPa(g) (14.5 to 1160 psig), or about 0.3 to about 2.5 MPa(g) (24 to 362.6 psig). The pressure is preferably sufficient to keep the reactants in the liquid phase. The residence time of the reactants in the reaction zone 12 is in the range of a few seconds to hours, or about 0.5 min to about 60 min, or about 1 min to about 60 min, or about 3 min to about 60 min.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1:1 to 100:1, for example, or in the range 2:1 to 50:1, or in the range 2:1 to 20:1.

The ionic liquid includes an organic cation and an anion. Suitable cations include, but are not limited to, nitrogen-containing cations and phosphorus-containing cations. The ionic liquid can comprise phosphonium based ionic liquids, pyridinium based ionic liquids, imidazolium based ionic liquids, ammonium based ionic liquids, pyrrolidinium based ionic liquids, and lactamium based ionic liquids. Ammonium based ionic liquids include trialkyl and tetra alkyl ammonium based ionic liquids.

In some embodiments, the anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br-$, $Ga_2Cl_6Br^-$, $Ga_3Cl_9Br^-$, $CuCl_2^-$, $Cu_2Cl_3^-$, $CU_3Cl_4^-$, $ZnCl_3^-$, $FeCl_3^-$, $FeCl_4^-$, $Fe_3Cl_7^-$, $PF_6^-$, and $BF_4^-$. In other embodiments, other anions could be used.

Returning to FIGS. 1 and 2, an effluent 20, including hydrocarbon conversion products, the ionic liquid catalyst, and unconverted reactants, catalyst promoter such as hydrogen chloride, organic chlorides, or other compounds, is passed from reactor 18 to a separation zone 22 having one or more separation vessels 24. In the separation zone 22, the effluent 20 separates into a hydrocarbon phase and an ionic liquid phase. This separation may be a phase separation as a result of the difference in the density of the hydrocarbon phase and the ionic liquid phase, although other methods could also be used, including for example, a coalescer material. Accordingly, an alkylate effluent stream 26 is sent to product recovery section 28 (discussed below). A spent ionic liquid catalyst stream 30 which typically includes some amount of conjunct polymer is also recovered from the separation zone 22. A first portion 32 of the spent ionic liquid catalyst stream 30 may be recycled directly to the reaction zone 12, while a second portion 34 of the spent ionic liquid catalyst stream 30 is passed to a regeneration zone 36 to remove at least some of the conjunct polymer from the ionic liquid catalyst.

The conjunct polymer is bound with the spent ionic liquid catalyst as an integrated compound. The conjunct polymer does not wash off from the spent ionic liquid catalyst via simple hydrocarbon solvent extraction. It is believed that the most efficient and effective process to reduce the conjunct polymer content in the spent ionic liquid catalyst is to convert the conjunct polymer species into extractable forms of hydrocarbons (i.e. light hydrocarbon gas or saturated hydrocarbon that is not very soluble in ionic liquid) and then separate or extract the hydrocarbons from the regenerated ionic liquid catalyst. During the regeneration process of the present invention, a portion of the conjunct polymer may be hydrocracked to a light material (C1-C4 hydrocarbons) which may be incorporated into the offgas, a portion may be hydrocracked to a liquid hydrocarbon stream which may be incorporated into the alkylate gasoline product, and/or a portion may be hydrocracked to HCl gas.

The regeneration zone 36 includes a regeneration reactor 38 for the regeneration reaction in which hydrogen from a hydrogen stream 40 is contacted with the conjunct polymer in the spent ionic liquid catalyst stream 30. As depicted the hydrogen stream 40 is combined with the second portion 34 of the spent ionic liquid catalyst stream 30 and the combined stream is heated and then injected into the regeneration reactor 38.

Regeneration processes that utilize one or more solid regeneration catalysts, as well as those that do not utilize solid regeneration catalysts may be used in accordance with the present invention. Exemplary regeneration processes are disclosed in U.S. Pat. Nos. 7,651,970, 7,691,771, and 7,825,055, and U.S. Patent Pub. No. 2017/0216827, the entirety of which are incorporated herein by reference. If the regeneration zone 36 does not utilize a solid regeneration catalyst, the regeneration reactor 38 provides for sufficient contact between the hydrogen and spent ionic liquid catalyst by agitating the liquids. By "agitating" it is meant that the regeneration reactor 38 increases the contacting between the spent ionic liquid catalyst (with conjunction polymer) and hydrogen by mixing, stirring, shaking, bubbling, with baffles, or any other action or structure increases the turbulence of the mixture to increase contacting between the spent ionic liquid catalyst and hydrogen. Suitable temperatures of an operating temperature of the regeneration reactor 38 are between approximately 93.3 and 343° C. (200 and 650° F.) or between approximately 148 and 260° C. (300 and 500° F.). Additionally, suitable operating pressures of the regeneration reactor 38 are between approximately 344.7 and 34,470 kPa (50 and 5,000 psig) or between approximately 4,139 to 10,345 kPa (600 and 1,500 psig).

As mentioned above, in various embodiments of the present processes, the amount of hydrogen is significantly reduced compared to conventional processes. Specifically, unlike convention processes in various embodiments of the present processes an amount of hydrogen is less than 550 SCF/BBL (97.96 $m^3/m^3$) of spent ionic liquid catalyst, or less than 500 SCF/BBL (89.05 $m^3/m^3$) of spent ionic liquid catalyst. Additionally, the amount of hydrogen may be between 550 and 45 SCF/BBL (97.96 and 8.015 $m^3/m^3$) of spent ionic liquid catalyst, or between 500 and 50 SCF/BBL (89.05 and 8.905 $m^3/m^3$) of spent ionic liquid catalyst.

From the regeneration reactor 38, a regenerated effluent 42 having a reduced amount of conjunct polymer is cooled and then passed to a separation vessel 44 which may be a flash drum. In the separation vessel 44, the regenerated effluent 42 is separated into a liquid phase including at least regenerated ionic liquid catalyst and a vapor phase including hydrogen and hydrogen chloride. Thus, a vapor phase stream 46 and a stream of regenerated ionic liquid catalyst 48 may be recovered from the separation vessel 44.

Unlike conventional processes in which the vapor phase stream 46 is combined with one or more streams separated from the alkylate effluent stream 26 to provide a high purity recycle hydrogen stream to the regeneration reactor and recycle hydrogen chloride to the alkylation reactor, in the present processes, the vapor phase stream 46 may be vented (as shown in FIG. 1) and passed to an HCl scrubber (not shown) due to the low amounts of HCl in the vapor phase stream 46. Thus, the hydrogen is used in a once-through process.

Alternatively, as shown in FIG. 2, all, or a portion of the vapor phase stream 46, is passed to a single stage compressor 50 which compresses the vapor phase stream 46 and provides a compressed vapor phase stream 52. The compressed vapor stream 52, including hydrogen and HCl, is combined with the second portion 34 of the spent ionic liquid catalyst stream 30. The presence of a small amount of HCl in the regeneration reactor 38 is beneficial, especially in regeneration processes that do not utilize a catalyst. Although the compressed vapor stream 52 is compressed in this embodiment of the present invention, unlike the conventional processes, in this embodiment, the compressed vapor stream 52 does not pass through a process for HCl separation between being compressed in the single stage compressor 50 and being combined with the spent ionic liquid catalyst stream 30.

Returning to both FIGS. 1 and 2, the stream regenerated ionic liquid catalyst 48 may be combined with the first portion 32 of the spent ionic liquid catalyst stream 30 and sent to a surge drum 54, a guard bed 56, and then recycled back to the reaction zone 12 as the ionic liquid catalyst stream 16. A makeup ionic liquid stream 58 may include one or more compounds and may be combined with the ionic liquid catalyst stream 16. A vent gas stream 60 from the surge drum 54 can be sent to a scrubber (not shown) to remove any HCl from the vent gas stream 60.

In the product recovery zone 28, the alkylate effluent stream 26 is separated into an alkylate product and a recycle hydrocarbon comprising unreacted hydrocarbons. Accordingly, for an alkylation reaction in which C3-C5 hydrocarbons are upgraded to more desirable compounds, in the depicted product recovery zone 28, the alkylate effluent stream 26 is heated and then passed to a first fractionation column 62 which is an isostripper column. In the isostripper column the components of the alkylate effluent stream 26 are separated into plurality of liquid streams that include a product stream 64, a normal butane side cut stream 66, and an isobutane sidecut stream 68. The product stream 64 comprises the desired alkylate from the reaction zone 12, the further processing of which is known in the art and not necessary for the practicing of the present invention. Similarly, the normal butane sidecut stream 66 is processed further as is known. The isobutane sidecut stream 68 contains, among other compounds, unreacted isobutane that is cooled and passed to a receiver 70 and then returned to the reaction zone 12 as a recycle stream, for example as the isoparaffin stream of isoparaffins 14 mentioned above.

The isostripper column also produces an overhead vapor stream 72 which includes C4 and lighter compounds, including some HCl. The overhead vapor stream 72 is cooled and passed to an isostripper overhead receiver 74. An isostripper overhead receiver vent gas 76 may be passed to a scrubber (not shown) to remove any HCl. A portion of an isostripper overhead receiver liquid stream 78 is passed back to the isostripper column as a reflux, while a second portion of the isostripper overhead receiver liquid stream 78 may be heated and passed to a depropanizer column 80.

In the depropanizer column 80, the compounds in the isostripper overhead receiver liquid stream 78 are separated. A depropanizer bottoms stream 82 may be combined with the isobutane sidecut stream 68 and passed to the receiver 70 to be recycled to the reaction zone 12 as discussed above. A depropanizer overhead stream 84 is cooled and passed to a depropanizer overhead receiver 86. A vent steam 88 from the depropanizer overhead receiver 86 may also be combined with the isobutane sidecut stream 68, cooled, and passed to the receiver 70 to be recycled to the reaction zone 12. A portion of a depropanizer overhead receiver bottom stream 90 may be refluxed back to the depropanizer column 80, while a second portion of the depropanizer overhead receiver bottom stream 90 may be passed to an HCl stripper column 92.

The HCl stripper column 92 separates the components of the depropanizer overhead receiver bottom stream 90 and provides an HCl stripper bottoms stream 94 which contains C3 and an HCl. HCl stripper overhead stream 96 which may be passed back to the depropanizer overhead receiver 86. It should be appreciated that this arrangement is merely exemplary and other configuration may be made by those of ordinary skill in the art. For example, it is contemplated that the depropanizer column is eliminated, and the isostripper overhead receiver liquid stream 78 may be passed directly to the HCl stripper column 92.

As discussed above, the present processes were based on the surprising discovery that the amount of hydrogen gas in the regeneration section can be significantly lowered. The below EXPERIMENTAL RESULTS demonstrate that the regeneration processes are effective with a lower amount of hydrogen.

EXPERIMENTAL RESULTS

Example 1: Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5NC_4H_9Al_2Cl_7$) ionic liquid catalyst is an example used in the present processes. The ionic liquid catalyst has the following composition:

| | |
|---|---|
| Al | 12.4 (wt. %) |
| Cl | 56.5 (wt. %) |
| C | 24.6 (wt. %) |
| H | 3.2 (wt. %) |
| N | 3.3 (wt. %) |

Example 2: Alkylation of C4 Olefin and Isobutane to Produce Alkylate Gasoline Evaluation of C4 olefins alkylation with isobutane was performed in a continuously stirred tank reactor using typical refinery mixed C4 olefin feed and isobutane. A 10:1 molar mixture of isobutane and olefin was fed to the reactor while vigorously stirring. An ionic liquid catalyst was fed to the reactor via a second inlet port targeting to occupy 5-6 vol % in the reactor. A small amount of n-butyl chloride was added to produce anhydrous HCl gas. The average residence time (combined volume of feeds and catalyst) was about 5 minutes. The outlet pressure was maintained at approximately 1380 kPa (200 psig) and the reactor temperature was maintained at 35° C. (95° F.) using external cooling.

The reactor effluent was separated with a gravity separator and then through a coalescer into a hydrocarbon phase and an ionic liquid catalyst phase. The hydrocarbon stream was further separated into multiple streams: a C3 stream containing HCl, a nC4 stream, a iC4 stream and an alkylate gasoline stream. The alkylate product had 94 Research Octane Number and 204° C. (400° F.) end point.

Example 3: Regeneration of Ionic Liquid Catalyst with Hydrogen Gas

The spent ionic liquid catalyst was sent to an on-line regeneration unit operated at 176.7° C. (350° F.) and 5,516 kPa (800 psig) and 0.15 LHSV without any solid regeneration catalyst. The hydrogen flow was varied in the range of 520 to 2,200 SCF $H_2$/BBL ionic liquid to examine the performance of the regeneration process as a function of hydrogen gas flow. To facilitate intimate contact between the spent ionic liquid catalyst with hydrogen gas, a bubble column reactor described in U.S. Pat. No. 9,802,186 was used. The hydrogenation reactor effluent was separated into gas and liquid stream. The conjunct polymer in the ionic liquid catalyst was converted to light hydrocarbon materials and HCl. The liquid stream containing liquid hydrocarbon and regenerated ionic liquid catalyst was sent to a catalyst surge drum and then to the alkylation reactor. The hydrogenation reactor offgas from the gas-liquid separation unit contained mostly hydrogen gas and several thousand ppm of HCl. The offgas also contained less than 10 vol % of C1-C6 light hydrocarbons, the bulk of light hydrocarbon being propane and isobutane.

Tables 1 and 2, below, show the regeneration process performance achieved in reducing the conjunct polymer content in spent ionic liquid catalyst at 162.8° C. (325° F.) and 176.7° C. (350° F.), respectively, at approximately 5,516 kPa (800 psig) in a bubble-column regeneration reactor as the amount of hydrogen gas fed to the regeneration reactor is reduced.

TABLE 1

Bubble-Column Regeneration of Spent Ionic Liquid Catalyst at 162.8° C. (325° F.) and 5,516 kPa (800 psig)

| | Hydrogen Flow | | |
|---|---|---|---|
| | 2,220 SCF $H_2$/BBL IL (395.4 $m^3/m^3$) | 1,110 SCF $H_2$/BBL IL (197.7 $m^3/m^3$) | 520 SCF $H_2$/BBL IL (92.6 $m^3/m^3$) |
| Conjunct Polymer Conversion (%) | 45 | 48 | 53 |
| $1^{st}$ Order Rate Constant ($hr_{-1}$) | 0.08 | 0.09 | 0.10 |

TABLE 2

Bubble-Column Regeneration of Spent Ionic Liquid Catalyst at 176.7° C. (350° F.) and 5,516 kPa (800 psig)

| | Hydrogen Flow | | |
|---|---|---|---|
| | 2,220 SCF $H_2$/BBL IL (395.4 $m^3/m^3$) | 1,110 SCF $H_2$/BBL IL (197.7 $m^3/m^3$) | 520 SCF $H_2$/BBL IL (92.6 $m^3/m^3$) |
| Conjunct Polymer Conversion (%) | 56 | 55 | 61 |
| $1^{st}$ Order Rate Constant ($hr_{-1}$) | 0.12 | 0.11 | 0.13 |

As will be appreciated based on the results shown in Table 1, the amount of hydrogen was lowered from 2,200 to 1,100 to 520 SCF/BBL IL (395.4 to 197.7 to 92.6 $m^3/m^3$) while surprisingly maintaining the same performance within error bars for conjunct polymer removal. The data in Table 2 shows that the reaction rate is higher at the higher temperature than Table 1 (176.7° C. (350° F.) vs. 162.8° C. (325° F.)). Again, at a constant reactor temperature, the regeneration performance is nearly identical when the hydrogen flow was lowered from 2,200 to 1,100 to 520 SCF/BBL IL. This effective and efficient performance of the regeneration reactor at such a low hydrogen flow is quite unexpected. Based on this data, it is believed that the amount of hydrogen can be further lowered to below 500 SCF/BBL IL (89.05 $m^3/m^3$). As discussed above, with the reduced amount of hydrogen, the various processes described above allow for the elimination of complex and expensive equipment.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a process for regenerating spent ionic liquid catalyst, the process comprising contacting spent ionic liquid catalyst with hydrogen in a reactor, the reactor operating at conditions sufficient to reduce an amount of conjunct polymer in the spent ionic liquid to provide a regenerated ionic liquid catalyst, wherein an amount of hydrogen is less than 550 SCF/BBL (97.96 $m^3/m^3$) of spent ionic liquid catalyst. An embodiment of the invention is one, any or all of prior embodiments in this paragraph up through the first embodiment in this paragraph, wherein the amount of hydrogen is between 550 and 45 SCF/BBL (97.96 and 8.015 $m^3/m^3$) of spent ionic liquid catalyst. An embodiment of the invention is one, any or all of prior embodiments in this paragraph up through the first embodiment in this paragraph, wherein the amount of hydrogen is less than 500 SCF/BBL (89.05 $m^3/m^3$) of spent ionic liquid catalyst. An embodiment of the invention is one, any or all of prior embodiments in this paragraph up through the first embodiment in this paragraph, wherein the amount of hydrogen is between 500 and 50 SCF/BBL (89.05 and 8.905 $m^3/m^3$) of spent ionic liquid catalyst. An embodiment of the invention is one, any or all of prior embodiments in this paragraph up through the first embodiment in this paragraph wherein an operating temperature of the reactor is between 93.3 and 343° C. (200 and 650° F.). An embodiment of the invention is one, any or all of prior embodiments in this paragraph up through the first embodiment in this paragraph wherein an operating pressure of the reactor is between 344.7 and 34,470 kPa (50 and 5,000 psig). An embodiment of the invention is one, any or all of prior embodiments in this paragraph up through the first embodiment in this paragraph wherein the contacting of the spent ionic liquid and the hydrogen occurs in the presence of a catalyst. An embodiment of the invention is one, any or all of prior embodiments in this paragraph up through the first embodiment in this paragraph wherein the contacting of the spent ionic liquid and the hydrogen occurs in the absence of a catalyst. An embodiment of the invention is one, any or all of prior embodiments in this paragraph up through the first embodiment in this paragraph wherein the contacting includes agitating a mixture of the spent ionic liquid and the hydrogen within the reactor.

A second embodiment of the invention is a process for regenerating spent ionic liquid catalyst by removing conjunct polymer from the spent ionic liquid catalyst, the process comprising passing a stream of spent ionic liquid catalyst stream to a regeneration zone, the regeneration zone comprising at least one reactor vessel and the stream of spent ionic liquid catalyst comprising conjunct polymer; passing a stream of hydrogen into the regeneration zone, wherein an amount of hydrogen passed to the regeneration zone comprises less than 550 SCF/BBL (97.96 $m^3/m^3$) of spent ionic liquid catalyst passed to the regeneration zone; contacting the conjunct polymer from the stream of spent ionic liquid catalyst with the hydrogen in the regeneration zone; and, recovering a regenerated ionic liquid catalyst stream comprising less conjunct polymer than the stream of spent ionic liquid catalyst. An embodiment of the invention is one, any or all of prior embodiments in this paragraph up through the second embodiment in this paragraph wherein the contacting of the spent ionic liquid and the hydrogen occurs in the presence of a catalyst. An embodiment of the invention is one, any or all of prior embodiments in this paragraph up through the second embodiment in this paragraph wherein the contacting of the spent ionic liquid and the hydrogen occurs in the absence of a catalyst. An embodiment of the invention is one, any or all of prior embodiments in this paragraph up through the second embodiment in this paragraph wherein the contacting includes agitating a mixture of the spent ionic liquid and the hydrogen within the reaction zone. An embodiment of the invention is one, any or all of prior embodiments in this paragraph up through the second embodiment in this paragraph comprising injecting the stream of hydrogen into the stream of spent ionic liquid catalyst to form a combined stream; and injecting the combined stream into the at least one reactor of the regeneration zone. An embodiment of the invention is one, any or all of prior embodiments in this paragraph up through the second embodiment in this paragraph, wherein the amount of hydrogen passed to the regeneration zone is between 550 and 45 SCF/BBL (97.96 and 8.015 $m^3/m^3$) of spent ionic liquid catalyst passed to the regeneration zone. An embodiment of the invention is one, any or all of prior embodiments in this paragraph up through the second embodiment in this paragraph, wherein the amount of hydrogen passed to the regeneration zone is less than 500 SCF/BBL (89.05 $m^3/m^3$) of spent ionic liquid catalyst passed to the regeneration zone. An embodiment of the invention is one, any or all of prior embodiments in this paragraph up through the second embodiment in this paragraph, wherein the amount of hydrogen passed to the regeneration zone is between 500 and 50 SCF/BBL (89.05 and 8.905 $m^3/m^3$) of spent ionic liquid catalyst passed to the regeneration zone. An embodiment of the invention is one, any or all of prior embodiments in this paragraph up through the second embodiment in this paragraph wherein an operating temperature of the reactor is between 93.3 and 343° C. (200 and 650° F.). An embodiment of the invention is one, any or all of prior embodiments in this paragraph up through the second embodiment in this paragraph wherein an operating pressure of the reactor is between 344.7 and 34,470 kPa (50 and 5,000 psig).

A third embodiment of the invention is a process comprising passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an alkylate effluent; separating the alkylate effluent from spent ionic liquid catalyst in a separation zone; passing a stream of the spent ionic liquid catalyst to a regeneration vessel in a regeneration zone, wherein the spent ionic liquid catalyst includes conjunct polymer; passing hydrogen into the regeneration vessel of the regeneration zone, wherein an amount of hydrogen passed to the regeneration zone comprises less than 550 SCF/BBL (97.96 m$^3$/m$^3$) of spent ionic liquid catalyst passed to the regeneration zone; contacting the hydrogen with the conjunct polymer in the regeneration vessel; and, passing a stream of regenerated ionic liquid catalyst from the regeneration zone to the reaction zone, wherein the regenerated ionic liquid catalyst comprises less conjunct polymer than the spent ionic liquid catalyst.

A fourth embodiment of the invention is a process for regenerating spent ionic liquid catalyst by removing conjunct polymer from the spent ionic liquid catalyst, the process comprising operating a reaction vessel under conditions sufficient to perform, in the presence of an ionic liquid catalyst, a hydrocarbon conversion reaction and provide a reaction effluent; separating the reaction effluent into a hydrocarbon phase and a spent ionic liquid catalyst, wherein the spent ionic liquid catalyst includes conjunct polymer; contacting the spent ionic liquid catalyst with hydrogen in a regeneration zone at conditions sufficient to reduce an amount of conjunct polymer in the spent ionic liquid catalyst to provide a regenerated effluent, separating the regenerated effluent into a liquid phase comprising regenerated ionic liquid catalyst and a vapor phase comprising hydrogen and hydrogen chloride; separating the hydrocarbon phase into a plurality of liquid hydrocarbon streams; and, isolating the vapor phase from the liquid hydrocarbon streams. An embodiment of the invention is one, any or all of prior embodiments in this paragraph up through the fourth embodiment in this paragraph further comprising removing the hydrogen chloride from the vapor phase in a scrubber. An embodiment of the invention is one, any or all of prior embodiments in this paragraph up through the fourth embodiment in this paragraph further comprising compressing a portion of the vapor phase in a single stage compressor to provide a compressed vapor phase; and, combining the compressed vapor phase with the spent ionic liquid catalyst, wherein the compressed vapor phase does not pass through a process for HCl separation between being compressed in the single stage compressor and being combined with the spent ionic liquid catalyst. An embodiment of the invention is one, any or all of prior embodiments in this paragraph up through the fourth embodiment in this paragraph wherein the hydrocarbon conversion reaction comprises an alkylation reaction. An embodiment of the invention is one, any or all of prior embodiments in this paragraph up through the fourth embodiment in this paragraph wherein the plurality of liquid hydrocarbon streams comprises at least one recycle stream to the reaction vessel, and one alkylate product stream. An embodiment of the invention is one, any or all of prior embodiments in this paragraph up through the fourth embodiment in this paragraph wherein the hydrocarbon phase is also separated into at least one vapor stream. An embodiment of the invention is one, any or all of prior embodiments in this paragraph up through the fourth embodiment in this paragraph wherein the at least one vapor stream is combined with the at least one recycle stream. An embodiment of the invention is one, any or all of prior embodiments in this paragraph up through the fourth embodiment in this paragraph, wherein the spent ionic liquid catalyst is contacted with the hydrogen in the regeneration zone in the presence of a catalyst. An embodiment of the invention is one, any or all of prior embodiments in this paragraph up through the fourth embodiment in this paragraph, wherein the spent ionic liquid catalyst is contacted with the hydrogen in the regeneration zone in the absence of a catalyst.

A fifth embodiment of the invention is a process for regenerating spent ionic liquid catalyst by removing conjunct polymer from the spent ionic liquid catalyst, the process comprising passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an effluent stream; separating the effluent stream in a separation zone into a hydrocarbon stream and a spent ionic liquid catalyst stream, wherein the spent ionic liquid catalyst stream includes conjunct polymer; passing a stream of the spent ionic liquid catalyst to a regeneration vessel in a regeneration zone; reducing an amount of the conjunct polymer in the spent ionic liquid catalyst with hydrogen in a regeneration vessel to provide a regeneration effluent comprising regenerated ionic liquid catalyst; passing a stream of the regeneration effluent to a separation vessel configured to separate the regenerated effluent into a liquid phase comprising the regenerated ionic liquid catalyst and a vent gas stream comprising hydrogen and hydrogen chloride; and, passing a recycle stream comprising the regenerated ionic liquid catalyst to the reaction zone. An embodiment of the invention is one, any or all of prior embodiments in this paragraph up through the fifth embodiment in this paragraph wherein the amount of the conjunct polymer is reduced with hydrogen in the presence of a catalyst. An embodiment of the invention is one, any or all of prior embodiments in this paragraph up through the fifth embodiment in this paragraph wherein the amount of the conjunct polymer is reduced with hydrogen in the absence of a solid regeneration catalyst. An embodiment of the invention is one, any or all of prior embodiments in this paragraph up through the fifth embodiment in this paragraph further comprising compressing a portion of the vent gas stream in a single stage compressor to provide a compressed vapor stream; and, passing the compressed vapor stream to the regeneration vessel, wherein the compressed vapor phase does not pass through a process for HCl separation between being compressed in the single stage compressor and being combined with the spent ionic liquid catalyst. An embodiment of the invention is one, any or all of prior embodiments in this paragraph up through the fifth embodiment in this paragraph further comprising venting a portion of the recycle stream before passing the regenerated ionic liquid catalyst to the reaction vessel. An embodiment of the invention is one, any or all of prior embodiments in this paragraph up through the fifth embodiment in this paragraph further comprising removing the hydrogen chloride from the vent gas stream in a scrubber.

A sixth embodiment of the invention is a process for regenerating spent ionic liquid catalyst by removing conjunct polymer from the spent ionic liquid catalyst, the process comprising passing an olefin stream of olefins to a reaction vessel in a reaction zone; passing an isoparaffin stream of isoparaffins to the reaction vessel in the reaction zone; passing a stream of ionic liquid catalyst to the reaction vessel in the reaction zone; operating the reaction vessel under conditions sufficient to perform an alkylation reaction between the olefins and the isoparaffins and provide an effluent stream; separating the effluent stream in a separation zone to provide a hydrocarbon stream and a spent ionic liquid catalyst stream, wherein the spent ionic liquid catalyst stream includes spent ionic liquid catalyst and conjunct polymer; passing the spent ionic liquid catalyst stream to a regeneration vessel in a regeneration zone; reducing an amount of the conjunct polymer in the spent ionic liquid catalyst with hydrogen in a regeneration vessel to provide a regeneration effluent; passing a stream of the regeneration effluent to a separation vessel configured to separate the regenerated effluent into a liquid phase comprising regenerated ionic liquid catalyst and a vent gas stream comprising hydrogen and hydrogen chloride; separating the hydrocarbon stream in a product recovery zone into a plurality of liquid hydrocarbon streams and at least one vapor stream; combining at least one of the liquid hydrocarbon stream and the at least one vapor stream to provide a combined recycle stream; and, passing the combined recycle stream to the reaction vessel in the reaction zone, wherein the at least one vapor stream does not pass through a process for HCl separation between being separated in the product recovery zone and being combined with the liquid hydrocarbon stream. An embodiment of the invention is one, any or all of prior embodiments in this paragraph up through the sixth embodiment in this paragraph wherein the product recovery zone comprises at least one distillation column configured to provide at least two liquid hydrocarbon streams and an overhead stream. An embodiment of the invention is one, any or all of prior embodiments in this paragraph up through the sixth embodiment in this paragraph further comprising passing the overhead stream to an HCl Stripper configured to provide at least one of the liquid hydrocarbon streams and the at least one vapor stream. An embodiment of the invention is one, any or all of prior embodiments in this paragraph up through the sixth embodiment in this paragraph further comprising, wherein the at least one liquid hydrocarbon stream from the product recovery zone is combined with the at least one vapor stream from the HCl Stripper. An embodiment of the invention is one, any or all of prior embodiments in this paragraph up through the sixth embodiment in this paragraph wherein the at least two liquid hydrocarbon streams comprise an alkylate stream and an isobutane recycle stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for regenerating a spent ionic liquid catalyst, the process comprising:
    contacting the spent ionic liquid catalyst with a hydrogen in a reactor, the reactor operating at conditions sufficient to reduce a conjunct polymer in the spent ionic liquid catalyst to provide a regenerated ionic liquid catalyst, wherein the reactor is a flow-through reactor, wherein an amount of the hydrogen is less than 97.96 $m^3/m^3$ of the spent ionic liquid catalyst.

2. The process of claim 1, wherein the amount of the hydrogen is between 97.96 and 8.015 $m^3/m^3$ of the spent ionic liquid catalyst.

3. The process of claim 1, wherein the amount of the hydrogen is less than 89.05 $m^3/m^3$ of the spent ionic liquid catalyst.

4. The process of claim 1, wherein the amount of the hydrogen is between 89.05 and 8.905 $m^3/m^3$ of the spent ionic liquid catalyst.

5. The process of claim 1 wherein an operating temperature of the reactor is between 93.3 and 343° C.

6. The process of claim 1 wherein an operating pressure of the reactor is between 344.7 and 34,470 kPa.

7. The process of claim 1 wherein the contacting of the spent ionic liquid catalyst and the hydrogen occurs in the presence of a solid regeneration catalyst.

8. The process of claim 1 wherein the contacting of the spent ionic liquid catalyst and the hydrogen occurs in the absence of a solid regeneration catalyst.

9. The process of claim 8 wherein the contacting includes agitating a mixture of the spent ionic liquid catalyst and the hydrogen within the reactor.

10. A process for regenerating a spent ionic liquid catalyst by removing a conjunct polymer from the spent ionic liquid catalyst, the process comprising:
    passing a stream of the spent ionic liquid catalyst to a regeneration zone, the regeneration zone comprising at least one reactor vessel and the stream of the spent ionic liquid catalyst comprising the conjunct polymer;
    passing a stream of a hydrogen into the regeneration zone, wherein an amount of the hydrogen passed to the regeneration zone comprises less than 97.96 $m^3/m^3$ of the spent ionic liquid catalyst passed to the regeneration zone, wherein the regeneration zone is a flow-through regeneration zone;
    contacting the conjunct polymer from the stream of the spent ionic liquid catalyst with the hydrogen in the regeneration zone; and,
    recovering a regenerated ionic liquid catalyst stream comprising less of the conjunct polymer than the stream of the spent ionic liquid catalyst.

11. The process of claim 10 wherein the contacting of the spent ionic liquid catalyst and the hydrogen occurs in the presence of a solid regeneration catalyst.

12. The process of claim 10 wherein the contacting of the spent ionic liquid catalyst and the hydrogen occurs in the absence of a solid regeneration catalyst.

13. The process of claim 12 wherein the contacting includes agitating a mixture of the spent ionic liquid catalyst and the hydrogen within the regeneration zone.

14. The process of claim 10 comprising:
    injecting the stream of the hydrogen into the stream of the spent ionic liquid catalyst to form a combined stream; and
    injecting the combined stream into the at least one reactor vessel of the regeneration zone.

15. The process of claim 10, wherein the amount of the hydrogen passed to the regeneration zone is between 97.96 and 8.015 $m^3/m^3$ of the spent ionic liquid catalyst passed to the regeneration zone.

16. The process of claim 10, wherein the amount of the hydrogen passed to the regeneration zone is less than 89.05 m³/m³ of the spent ionic liquid catalyst passed to the regeneration zone.

17. The process of claim 10, wherein the amount of the hydrogen passed to the regeneration zone is between 89.05 and 8.905 m³/m³ of the spent ionic liquid catalyst passed to the regeneration zone.

18. The process of claim 10 wherein an operating temperature of the at least one reactor vessel is between 93.3 and 343° C.

19. The process of claim 10 wherein an operating pressure of the at least one reactor vessel is between 344.7 and 34,470 kPa.

20. An alkylation process comprising:
passing an olefin stream of olefins to a reaction vessel in a reaction zone;
passing an isoparaffin stream of isoparaffins to the reaction vessel in the reaction zone;
passing a catalyst stream of an ionic liquid catalyst to the reaction vessel in the reaction zone;
operating the reaction vessel under conditions sufficient to perform an alkylation reaction between the olefins and the isoparaffins and provide an alkylate effluent;
separating the alkylate effluent from a spent ionic liquid catalyst in a separation zone;
passing a first stream of the spent ionic liquid catalyst to a regeneration vessel in a regeneration zone, wherein the spent ionic liquid catalyst includes a conjunct polymer;
passing a hydrogen into the regeneration vessel of the regeneration zone, wherein an amount of the hydrogen passed to the regeneration zone comprises less than 97.96 m³/m³ of the spent ionic liquid catalyst passed to the regeneration zone, wherein the regeneration zone is a flow-through regeneration zone;
contacting the hydrogen with the conjunct polymer in the regeneration vessel; and,
passing a regenerated stream of a regenerated ionic liquid catalyst from the regeneration zone to the reaction zone, wherein the regenerated ionic liquid catalyst comprises less of the conjunct polymer than the spent ionic liquid catalyst.

* * * * *